United States Patent
Bruder et al.

(10) Patent No.: US 6,596,270 B2
(45) Date of Patent: Jul. 22, 2003

(54) METHODS OF ADMINISTERING ADENOVIRAL VECTORS

(75) Inventors: Joseph T. Bruder, Ijamsville, MD (US); Imre Kovesdi, Rockville, MD (US)

(73) Assignee: GenVec, Inc., Gaithersburg, MD (US)

( * ) Notice: Subject to any disclaimer, the term of this patent is extended or adjusted under 35 U.S.C. 154(b) by 98 days.

(21) Appl. No.: 09/835,683

(22) Filed: Apr. 16, 2001

(65) Prior Publication Data

US 2002/0013286 A1 Jan. 31, 2002

Related U.S. Application Data

(63) Continuation-in-part of application No. PCT/US99/24133, filed on Oct. 15, 1999, which is a continuation-in-part of application No. 09/174,508, filed on Oct. 16, 1998.

(51) Int. Cl.[7] .................. A61K 35/00; A61K 48/00; A61K 39/235; C12N 15/63
(52) U.S. Cl. .................. 424/93.2; 514/44; 435/320.1; 435/325; 424/69.1; 424/93.1; 424/199.1; 424/233.1
(58) Field of Search .................. 514/44; 435/320.1, 435/455, 69.1, 69.6, 456; 424/93.1, 199.1, 233.1

(56) References Cited

U.S. PATENT DOCUMENTS 5,585,362 A  12/1996  Wilson et al. .................. 514/44

FOREIGN PATENT DOCUMENTS

| WO | WO 95/34671 A | 12/1995 |
| WO | WO 96/40272 A | 12/1996 |
| WO | WO 97/06826 A | 2/1997 |
| WO | WO 98/35028 A | 8/1998 |

OTHER PUBLICATIONS

Barr et al., *Gene Ther.*, 2 (2), 151–155 (Mar. 1995).
Bennett et al., *Hum. Gene Ther.*, 7, 1763–1769 (Sep. 10, 1996).
Berkner et al., *J. Virol.*, 61 (4), 1213–1220 (Apr. 1987).
Chen et al., *Gene Ther.*, 7 (7), 587–595 (Apr. 2000).
Christ et al., *Immunol. Lett.*, 57 (1–3), 19–25 (Jun. 1, 1997).
Curiel et al., *Hum. Gene Ther.*, 3 (2), 147–154 (Apr. 1992).
Davidson et al., *J. Virol.*, 61 (4), 1226–1239 (Apr. 1987).
Gilgenkrantz et al., *Hum. Gene Ther.*, 6 (10), 1265–1274 (Oct. 1995).
Ilan et al., *PNAS USA*, 94, 2587–2592 (Mar. 1997).
Jaffe et al., *Nature Genet.*, 1, 372–378 (Aug. 1992).
Kay et al., *Nature Genet.*, 11, 191–197 (Oct. 1995).
Lei et al., *Hum. Gene Ther.*, 7, 2273–2279 (Dec. 1, 1996).
Li et al., *Cardiovascular Res.*, 30, 97–105 (1995).
Mack et al., *Hum. Gene Ther.*, 8, 99–109 (Jan. 1, 1997).
Mansour et al., *Mol. Cell Biol.*, 6, 2684–2694 (Jul. 1986).
Michou et al., *Gene Ther.*, 4 (5), 473–482 (May 1997).
Svensson et al., *Hum. Gene Ther.*, 8, 1797–1806 (Oct. 10, 1997).
Tripathy et al., *Nature Med.*, 2 (5), 545–550 (May 1996).
Wilson et al., *Nature Med.*, 1 (9), 887–889 (Sep. 1995).
Yang et al., *Hum. Mol. Genet.*, 5 (11), 1703–1712 (Nov. 1996).
Yang et al., *J. Virol.*, 69 (4), 2004–2014 (Apr. 1995).
Yang et al., *J. Virol.*, 70 (9), 6370–6377 (Sep. 1996).

*Primary Examiner*—Ram R. Shukla
(74) *Attorney, Agent, or Firm*—Leydig, Voit & Mayer, Ltd

(57) ABSTRACT

The present invention provides methods for administering an adenoviral gene transfer vector comprising an exogenous gene to an animal. One method involves utilizing systemic neutralizing antibodies to neutralize the adenoviral gene transfer vector outside a targeted muscle. Another method involves the repeat administration of an adenoviral gene transfer vector to a skeletal muscle.

12 Claims, No Drawings

METHODS OF ADMINISTERING ADENOVIRAL VECTORS

This application is a continuation-in-part of international patent application no. PCT/US99/24133, filed Oct. 15, 1999, which is a continuation-in-part of U.S. patent application Ser. No. 09/174,508, filed Oct. 16, 1998.

TECHNICAL FIELD OF THE INVENTION

The present invention relates to methods for administering gene products to animals using adenoviral vectors.

BACKGROUND OF THE INVENTION

Modified viruses have proven convenient vector systems for investigative and therapeutic gene transfer applications, and adenoviral vector systems present several advantages for such uses. Adenoviruses are generally associated with benign pathologies in humans, and the 36 kb of the adenoviral genome has been extensively studied. Adenoviral vectors can be produced in high titers (e.g., about $10^{13}$ pfu), and such vectors can transfer genetic material to nonreplicating, as well as replicating, cells; in contrast with, e.g., retroviral vectors, which only transfer genetic material to replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.* 3: 147–154 (1992)). Additionally, adenoviruses generally do not integrate into the host cell chromosome, but rather are maintained as a linear episome, thus minimizing the likelihood that a recombinant adenovirus will interfere with normal cell function. Aside from being a superior vehicle for transferring genetic material to a wide variety of cell types, adenoviral vectors represent a safe choice for gene transfer, a particular concern for therapeutic applications.

A variety of recombinant adenoviral vectors have been described. Most of the vectors in use today derive from the adenovirus serotype 5 (Ad5), a member of subgroup C. An exogenous gene of interest typically is inserted into the early region 1 (E1) of the adenovirus. Disruption of the E1 region decreases the amount of viral proteins produced by both of the early regions (DNA binding protein) and late regions (penton, hexon, and fiber proteins), preventing viral propagation. Replication-deficient adenoviral vectors require growth in either a complementary cell line or in the presence of an intact helper virus, which provides, in trans, the essential E1 functions (Berker et al., *J. Virol.* 61: 1213–1220 (1987); Davidson et al., *J. Virol.* 61: 1226–1239 (1987); Mansour et al., *Mol. Cell Biol.* 6: 2684–2694 (1986)). More recently, adenoviral vectors deficient in both E1 and the early region 4 (E4) have been used to substantially abolish expression of viral proteins. In order to insert the larger genes (up to 8 kb) into the adenoviral genome, adenoviral vectors additionally deficient in the nonessential early region 3 (E3) and the early region 2 (E2) can be used. Multiply deficient adenoviral vectors are described in published PCT patent application WO 95/34671.

One limitation of adenoviral vector systems is the ability of the adenoviral vector to transduce a wide variety of proliferating and quiescent cells (Michou et al., *Gene Ther.* 4: 473–482 (1997)). This ability, while a benefit in transducing the target area, is a limitation when the adenoviral vector "leaks" out of the targeted area and transduces other cells it contacts. Tranduction of the surrounding cells is a serious problem when the gene product encoded by the adenoviral vector is harmful, toxic, or otherwise undesirable with respect to these non-targeted areas.

Another limitation of the adenoviral vector system is the cellular and humoral immune response generated within the host animal. Initial administration elicits a reaction from both $CD8^+$ and $CD4^+$ T lymphocytes, which eliminate virus infected cells within 28 days after infection, limiting the duration of the transgene expression. In addition, neutralizing antibodies produced by B lymphocytes in cooperation with $CD4^+$ cells inhibit the effectiveness of repeat administration of the adenoviral vector. Proliferation and specificity of the antibodies to the adenoviral vectors occurs through interactions among the adenoviral vector, B-cell surface immunoglobulins and activated $CD4^+$ surface proteins (particularly CD40 ligand (CD40L), which binds CD40 on the surface of B cells) (Yang et al., *J. Virol.* 69: 2004 (1995)).

Attempts to circumvent the humoral immune response to allow repeat administration of the adenoviral vector have met with limited success. These attempts have focused in two areas: immunosuppression and alteration of the adenoviral vector. Several groups have experimented with various immunosuppressant drugs or antibodies specific for $CD4^+$, CD40L, or CTLA4Ig to reduce the adenovirus-specific humoral immune response (Lee et al., *Hum. Gene Ther.* 7: 2273 (1996) ($CD4^+$); Yang et al., *J. Virol.* 70: 6370 (1996) (CD40L); Kay et al., *Nature Gen.* 11: 191 (1995) (CTLA4Ig)). Although some of these results have been encouraging, there is a substantial risk associated with systemic immune suppression in a clinical setting. Alteration of the adenoviral vector is time consuming and has not been entirely successful in sufficiently attenuating the immune response. Limited readministration of the adenoviral vector has been accomplished when adenoviral vectors of different serotypes within the same subgroup are used; however, persistence of expression of the transgene was not comparable to the initial administration (Mack et al., *Hum. Gene Ther.* 8: 99–109 (1997)).

Accordingly, there is a need for improved methods of administering adenoviral vectors to animals, particularly, to prevent leakage of the adenoviral vector from the target area and to circumvent the humoral immune response elicited by adenoviral vectors. The present invention provides such methods. This and other advantages of the present invention, as well as additional inventive features, will be apparent from the description of the invention provided herein.

BRIEF SUMMARY OF THE INVENTION

The present invention provides a method of targeting a gene product to a particular muscle of an animal. The method comprises inducing in an animal systemic neutralizing antibodies to an adenoviral gene transfer vector and administering the adenoviral gene transfer vector comprising an exogenous gene encoding a gene product to a particular muscle of the animal. Administration is such that the exogenous gene is expressed and the gene product is produced in the particular muscle of the animal and the adenoviral gene transfer vector is neutralized outside of the particular muscle of the animal by the systemic neutralizing antibodies.

The present invention further provides a method of producing a gene product in a skeletal muscle of an animal. The method comprises initially administering an adenoviral vector to a skeletal muscle of an animal, and, at least seven days after administration, subsequently administering an adenoviral gene transfer vector comprising an exogenous gene encoding a gene product to the skeletal muscle of the animal. Administration is such that the exogenous gene is expressed and the gene product is produced in the skeletal muscle of the animal.

The invention may best be understood with reference to the following detailed description.

DETAILED DESCRIPTION OF THE INVENTION

The present invention provides methods useful in the administration of gene products to animals using adenoviral gene transfer vectors. The ability to target an adenoviral vector and to administer repeatedly a therapeutic adenoviral vector in a clinical setting is useful in improving treatment efficacy and in enabling the treatment of diseases. This invention provides a method to limit the infection of non-target tissue following administration of an adenoviral vector to a particular muscle of an animal. The vector targeting potential is useful for cardiac, particularly, endocardial, administration, as the risk of misinjection of the adenoviral vector is high. As adenoviral vectors cannot be readministered systemically, the present invention also provides a method for repeat administration of an adenoviral gene transfer vector comprising an exogenous gene to the skeletal muscle of an animal.

The term "exogenous gene," as it is used herein, refers to any gene in an adenoviral gene transfer vector that is not native to the adenovirus that comprises the adenoviral vector. The gene includes a nucleic acid sequence encoding a gene product operably linked to a promoter. Any portion of the gene can be non-native to the adenovirus that comprises the adenoviral gene transfer vector. For example, the gene can comprise a non-native nucleic acid sequence encoding a gene product operably linked to a native promoter, or a native nucleic acid sequence encoding a gene product operably linked to a non-native promoter or in a non-native location within the adenoviral vector. It should be appreciated that the exogenous gene can be any gene encoding an RNA or protein of interest to the skilled artisan. Therapeutic genes, genes encoding a protein that is to be studied in vitro and/or in vivo, antisense nucleic acids, and modified viral genes are illustrative of possible exogenous genes.

The term "adenoviral gene transfer vector," as it is used herein, refers to any adenoviral vector with an exogenous gene encoding a gene product inserted into its genome. The vector must be capable of replicating and being packaged when any deficient essential genes are provided in trans. An adenoviral vector desirably contains at least a portion of each terminal repeat required to support the replication of the viral DNA, preferably at least about 90% of the full ITR sequence, and the DNA required to encapsidate the genome into a viral capsid. Many suitable adenoviral vectors have been described in the art.

The adenoviral gene transfer vector is preferably deficient in at least one gene function required for viral replication. Preferably, the adenoviral gene transfer vector is deficient in at least one essential gene function of the E1 region of the adenoviral genome, particularly the E1a region, more preferably, the vector is deficient in at least one essential gene function of the E1 region and part of the E3 region (e.g., an Xba I deletion of the E3 region) or, alternatively, the vector is deficient in at least one essential gene function of the E1 region and at least one essential gene function of the E4 region. However, adenoviral gene transfer vectors deficient in at least one essential gene function of the E2a region and adenoviral gene transfer vectors deficient in all of the E3 region also are contemplated here and are well-known in the art. Suitable replication-deficient adenoviral gene transfer vectors are disclosed in International Patent Applications WO 95/34671 and WO 97/21826. For example, suitable replication-deficient adenoviral gene transfer vectors include those with a partial deletion of the E1a region, a partial deletion of the E1b region, a partial deletion of the E2a region, and a partial deletion of the E3 region. Alternatively, the replication-deficient adenoviral gene transfer vector can have a deletion of the E1 region, a partial deletion of the E3 region, and a partial deletion of the E4 region.

It should be appreciated that the deletion of different regions of the adenoviral gene transfer vector can alter the immune response of the mammal, in particular, deletion of different regions can reduce the inflammatory response generated by the adenoviral gene transfer vector. Furthermore, the adenoviral gene transfer vector's coat protein can be modified so as to decrease the adenoviral gene transfer vector's ability or inability to be recognized by a neutralizing antibody directed against the wild-type coat protein, as described in International Patent Application WO 98/40509. Other suitable modifications to the adenoviral gene transfer vector are described in U.S. Pat. Nos. 5,559,099; 5,731,190; 5,712,136; and 5,846,782 and International Patent Applications WO 97/20051, WO 98/07877, and WO 98/54346.

Adenoviral gene transfer vectors can be specifically targeted through a chimeric adenovirus coat protein comprising a nonnative amino acid sequence, wherein the chimeric adenovirus coat protein directs entry into a specific cell of an adenoviral gene transfer vector comprising the chimeric adenovirus coat protein that is more efficient than entry into a specific cell of an adenoviral gene transfer vector that is identical except for comprising a wild-type adenovirus coat protein rather than the chimeric adenovirus coat protein. The chimeric adenovirus coat protein comprising a nonnative amino acid sequence can serve to increase efficiency by decreasing non-target cell transduction by the adenoviral gene transfer vector. The nonnative amino acid sequence of the chimeric adenovirus coat protein, which comprises from about 3 amino acids to about 30 amino acids, can be inserted into or in place of an internal coat protein sequence, or, alternatively, the nonnative amino acid sequence can be at or near the C-terminus of the chimeric adenovirus coat protein. The chimeric adenovirus coat protein can be a fiber protein, a penton base protein, or a hexon protein. In addition, the nonnative amino acid sequence can be linked to the chimeric adenovirus coat protein by a spacer sequence of from about 3 amino acids to about 30 amino acids. Targeting through a chimeric adenovirus coat protein is described generally in U.S. Pat. Nos. 5,559,099; 5,712,136; 5,731,190; 5,770,440; 5,871,726; and 5,830,686 and International Patent Applications WO 96/07734, WO 98/07877, WO 97/07865, WO 98/54346, WO 96/26281, and WO 98/40509. An adenoviral gene transfer vector that comprises a chimeric coat protein comprising a nonnative amino acid sequence in accordance with U.S. Pat. No. 5,965,541 or WO 97/20051, such as one that comprises polylysine as the nonnative amino acid sequence, can be used to re-administer an exogenous gene encoding a gene product to a particular muscle of an animal. The use of such a vector to repeat administration can result in a higher level of expression of the gene product as compared to an adenoviral vector in which the corresponding adenoviral coat protein has not been modified to comprise a nonnative amino acid sequence, such as polylysine.

The exogenous gene can be inserted into any suitable region of the adenoviral gene transfer vector as an expression cassette. Preferably, the DNA segment is inserted into the E1 region of the adenoviral gene transfer vector.

Whereas the DNA segment can be inserted as an expression cassette in any suitable orientation in any suitable region of the adenoviral gene transfer vector, preferably, the orientation of the DNA segment is from right to left. By the expression cassette having an orientation from right to left, it is meant that the direction of transcription of the expression cassette is opposite that of the region of the adenoviral gene transfer vector into which the expression cassette is inserted.

In one embodiment, the present invention provides a method of targeting a gene product to a particular muscle of an animal. The method comprises inducing in an animal systemic neutralizing antibodies to an adenoviral gene transfer vector and then administering the adenoviral gene transfer vector comprising an exogenous gene encoding a gene product to a particular muscle of the animal. Administration is such that the exogenous gene is expressed and the gene product is produced in the particular muscle of the animal and the adenoviral gene transfer vector is neutralized outside of the particular muscle of the animal.

The present invention can be practiced with any suitable animal, preferably the present invention is practiced with a mammal, more preferably, a human. Additionally, the adenoviral gene transfer vector can be administered to any suitable muscle of the animal.

Any suitable method can be used to induce systemic neutralizing antibodies to the adenoviral gene transfer vector. Desirably, an antigen is administered to the animal to produce systemic neutralizing antibodies to the adenoviral gene transfer vector. This antigen can be the same as the adenoviral gene transfer vector, but preferably, it is the same as the adenoviral gene transfer vector, except that it does not contain an exogenous gene (i.e., a null vector). The antigen also can be administered by any suitable method. Depending on the antigen, administration can be to any suitable area of the animal. In order to induce the systemic neutralizing antibodies, the antigen can be administered any number of suitable times, e.g., once, twice, or more.

Using a null vector, the antigen can be administered systemically (rather than to the target muscle) to prevent any damage to the particular muscle. Systemic administration can be accomplished through intravenous injection, either bolus or continuous, or any other suitable method.

Administration of the antigen produces circulating neutralizing antibodies. While not wishing to be bound by any particular theory, it is believed that when the adenoviral gene transfer vector is administered to the particular muscle of the animal, some of the adenoviral particles escape the muscle. These adenoviral particles are then neutralized by the antibodies circulating throughout the animal such that significantly less (and preferably substantially no) gene product is produced outside the particular muscle. The amount of gene product produced outside the particular muscle of administration in the animal is preferably at least 90% less (more preferably at least 99% less, and most preferably at least 99.9% less) than the production of the gene product outside the particular muscle of administration in a naive animal of the same species as the animal after administration of the adenoviral gene transfer vector comprising an exogenous gene. A naive animal is one that does not have circulating neutralizing antibodies to the adenoviral gene transfer vector.

Methods are known in the art for comparing the amount of gene product outside the muscle that is the site of administration in an animal with systemic neutralizing antibodies with the amount of gene product outside the same muscle that is the site of administration in a naive animal. For example, the comparison can be made at the same time after administration of the adenoviral gene transfer vector and between the same sites of the two animals.

Neutralization of adenoviral particles outside of the particular muscle prevents production of the exogenous gene carried in the adenoviral gene transfer vector. This is extremely useful in situations where the exogenous gene is harmful, or toxic, to the animal when present in areas other than the particular muscle of administration. An example of this is vascular endothelial growth factor (VEGF protein), which mediates vascular growth. While vascular growth is desirable in the heart to repair damaged cardiac muscle, growth outside the heart can lead to severe problems, including blindness and increased aggressiveness of tumor cells.

In view of the above, the method can further comprise subsequently repeating the administration of an adenoviral gene transfer vector comprising the exogenous gene encoding the gene product to the particular muscle of the animal. When the administration is repeated, the adenoviral gene transfer vector comprising the exogenous gene encoding the gene product preferably further comprises a chimeric adenoviral coat protein comprising a nonnative amino acid sequence, wherein the chimeric adenoviral coat protein directs entry of the vector into cells more efficiently than a vector that is otherwise identical, except for comprising a corresponding wild-type adenoviral coat protein (see, e.g., U.S. Pat. No. 5,965,541 or WO 97/20051). Preferably, the nonnative amino acid sequence consists essentially of polylysine, such as from about 3 to about 30 lysines.

In another embodiment, the present invention provides a method of producing a gene product in a skeletal muscle of an animal. The method comprises initially administering an adenoviral vector to a skeletal muscle of an animal, and, at least seven days after, subsequently administering an adenoviral gene transfer vector comprising an exogenous gene encoding a gene product to the skeletal muscle of the animal. Administration is such that the exogenous gene is expressed and the gene product is produced in the skeletal muscle of the animal.

Any suitable animal can be used; however, preferably, the animal is a mammal, more preferably, a human. In the context of the present invention, the adenoviral vector initially administered to the skeletal muscle of the animal can be the same as, or different from, the adenoviral gene transfer vector comprising an exogenous gene encoding a gene product subsequently administered at least seven days after the initial administration.

After subsequent administration of the adenoviral gene transfer vector comprising an exogenous gene, production of the gene product in the muscle of the animal is desirably at least 1% of (such as at least 10% of, preferably at least 50% of, more preferably at least 80% of, and most preferably, the same as or substantially the same as) production of the gene product after initial administration of the same adenoviral gene transfer vector containing the exogenous gene. Methods for comparing the amount of gene product produced in the muscle of administration are known in the art. The comparison can be made at the same time after the initial and subsequent administrations of the adenoviral gene transfer vector.

While not wishing to be bound by any particular theory, it is believed that the level of gene product produced in the skeletal muscle of an animal after the second or subsequent administration to the muscle can be substantially similar to that of the first or preceding administration because neutralizing antibodies, which are produced by the first or preceding administration, cannot readily penetrate the muscle and destroy the adenoviral gene transfer vector. When the neutralizing antibody response is boosted with two or more initial administrations of the adenoviral vector before the subsequent administration of the adenoviral gene transfer vector comprising the exogenous gene, the level of gene product produced in the skeletal muscle of administration may be lowered, yet still sufficient to produce a therapeutic or prophylactic effect.

In view of the above, the method can further comprise subsequently repeating the administration of an adenoviral gene transfer vector comprising the exogenous gene encoding the gene product to the skeletal muscle of the animal. When the administration is repeated, the adenoviral gene transfer vector comprising the exogenous gene encoding the gene product preferably further comprises a chimeric adenoviral coat protein comprising a nonnative amino acid sequence, wherein the chimeric adenoviral coat protein directs entry of the vector into cells more efficiently than a vector that is otherwise identical, except for comprising a corresponding wild-type adenoviral coat protein (see, e.g., U.S. Pat. No. 5,965,541 or WO 97/20051). Preferably, the nonnative amino acid sequence consists essentially of polylysine, such as from about 3 to about 30 lysines.

To facilitate the administration of adenoviral vectors, they can be formulated into suitable pharmaceutical compositions. Generally, such compositions include the active ingredient (i.e., the adenoviral vector) and a pharmacologically acceptable carrier. Such compositions can be suitable for delivery of the active ingredient to a patient for medical application, and can be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention can be formulated in a conventional manner using one or more pharmacologically or physiologically acceptable carriers comprising excipients, as well as optional auxiliaries, which facilitate processing of the active compounds into preparations which can be used pharmaceutically. Proper formulation is dependent upon the route of administration chosen. Thus, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

Those of ordinary skill in the art can easily make a determination of the proper dosage of the adenoviral gene transfer vector. Generally, certain factors will impact the dosage that is administered; although the proper dosage is such that, in one context, the exogenous gene is expressed and the gene product is produced in the particular muscle of the mammal. Preferably, the dosage is sufficient to have a therapeutic and/or prophylactic effect on the animal. The dosage also will vary depending upon the exogenous gene to be administered. Specifically, the dosage will vary depending upon the particular muscle of administration, including the specific adenoviral vector, exogenous gene and/or promoter utilized. For purposes of considering the dose in terms of particle units (pu), also referred to as viral particles, it can be assumed that there are 100 particles per particle forming unit (pfu) (e.g., $1 \times 10^{12}$ pfu is equivalent to $1 \times 10^{14}$ pu).

The present inventive methods are useful in the context of the treatment of animals, e.g., medical treatment. In addition, the present inventive methods are useful in the production of gene products, e.g., in vivo protein production (which can entail subsequent protein recovery) as well as in research, e.g., investigation of gene expression, adenoviral targeting, and the like.

EXAMPLES

The present invention is further described in the following examples. These examples serve only to illustrate the invention and are not intended to limit the scope of the invention in any way.

Adenoviral Vectors

The E1-, E3-deleted adenovirus vector, AdZ, expresses β-gal from the cytomegalovirus (CMV) promoter oriented from left to right and carries the simian virus 40 poly A sequences from an expression cassette inserted at the site of the E1 deletion. AdF and AdL are similar to AdZ except the CMV promoter drives the expression of green fluorescent protein and luciferase, respectively. AdNull contains the CMV promoter and simian virus 40 poly A sequences in place of the E1 region and does not express any exogenous genes. AdE4Null is similar to AdNull, except the E4 region is deleted and a non-functional β-glucuronidase gene is inserted. AdhβActin.L expresses luciferase from an expression cassette containing the 4.3 kb human β-actin promoter pointing left and the simian virus 40 poly A sequences. pAdRSV.L and AdMCK.L drive luciferase expression from the Rous sarcoma virus or the 3.3 kb muscle creatine kinase promoter, respectively.

All adenovirus vectors contain the dl324 E3 deletion and were generated using shuttle vectors as previously described (Bruder et al., *J. Virol.* 71(10): 7623–28 (1997); Chinnadurai et al., J. Virol. 32(2): 623–28 (1979)). Briefly, the shuttle vectors were linearized at a unique restriction site adjacent to the left end inverted terminal repeat (ITR) and cotransfected into 293 cells with ClaI digested adenovirus DNA. Virus generated by recombination between the shuttle vector and the adenovirus DNA was plaque purified and propagated on 293 cells (Graham et al., *J. Gen. Virol.* 36: 59–77 (1977)). Viruses were purified from infected cells at two days after vector administration by three freeze-thaw cycles followed by three successive bandings on CsCl gradients. Purified virus was dialyzed against a buffer containing 10 mM Tris (pH 7.8), 150 mM NaCl, 10 mM $MgCl_2$ and 3% sucrose and stored at −70° C. until use. All viruses were tested and found to have replication-competent adenovirus (RCA) levels of less than 1 in $1 \times 10^7$ pfu.

Animals

Female Balb/c and C57BL/6 mice were obtained from Charles River (Wilmington, Mass.) at six to eight weeks of age. Prior to administration, mice were anesthetized with a 0.1 ml intraperitoneal injection of ketamycin and rhompin (three parts water one part ketamycin/rhompin dilution).

Adenoviral vectors were administered intramuscularly (im) in a 50 μl volume. At the indicated times post-administration, mice were given an intraperitoneal injection of a terminal dose of anesthetic. The gastrocnemius muscles and livers were removed and washed quickly with PBS and flash-frozen in liquid nitrogen, ground with a mortar and pestle, aliquoted, and stored at −80° C. until use. Intravenous (iv) administration was performed by exposing the right jugular vein after making a supraclavicular incision and the vectors were injected by using a 30-gauge needle over a period of two minutes.

Neutralizing Antibodies

Neutralizing antibody titers were determined by analyzing the ability of serum antibody to inhibit infection of AdF on AE25 cells. AE25 cells were inoculated at $2 \times 10^4$ per well on flat bottom 96 well plates and grown for 18 to 24 hours at 37° C. A series of two-fold dilutions of the serum samples were incubated with AdF at a multiplicity of infection of 3 follicle forming units (ffu)/cell for one hour at 37° C. in minimal DMEM medium. This mixture was incubated with AE25 cells for one hour at 37° C., 100 μl of complete medium were added and the cells were cultured overnight. The neutralizing antibody titer was scored as the reciprocal of the last dilution where a 50% reduction in green cells (infected cells) was observed.

Enzyme Activity

Pulverized muscle or liver tissue was lysed in 1× Reporter Lysis Buffer (Promega Corp., Madison, Wis.) and protein determinations were made using the Bradford reagent. Protein samples were used to measure β-gal activity with the β-gal reporter gene assay system (Tropix, Bedford, Mass.).

Example 1

This example demonstrates production of neutralizing antibodies in response to adenovirus infection. Further demonstrated is production of a gene product by administration of an adenoviral gene transfer vector comprising the exogenous gene.

To determine the kinetics of adenovirus neutralizing antibody production following im delivery, mice were immunized with $1 \times 10^{10}$ pu of three different adenovirus vectors. Serum samples were taken at various times post-infection and adenovirus neutralizing antibody titers were measured. The neutralizing antibody response was detectable at 10 days and peaked between 14 and 21 days post-infection. Adenovirus neutralizing antibody titers dropped off significantly by day 56, thus demonstrating production of neutralizing antibodies in response to adenovirus infection.

Development of the humoral response to adenovirus infection is dependent on the dose and route of administration. To determine the minimal dose of vector that results in the production of neutralizing antibodies when delivered by the im route, mice were immunized with escalating doses of AdRSV.L, described above. Doses ranged from $10^2$ to $10^{10}$ pu. The first evidence of neutralizing antibody production was at a dose of $10^7$ pu. This was also the minimum dose where detectable luciferase expression from the vector was observed in muscle tissue. An immunizing dose of $10^8$ pu resulted in an increase in both luciferase expression and in neutralizing antibody production, thus demonstrating production of a gene product by administration of an adenoviral gene transfer vector comprising the exogenous gene.

Example 2

This example illustrates use of the present inventive method of targeting production of a gene product to a particular muscle in an animal, as well as the present inventive method of repeat administration to produce a gene product in a skeletal muscle of an animal. In particular, systemic neutralizing antibodies to an adenoviral vector were induced in an animal, and then the adenoviral vector comprising an exogenous gene encoding a gene product was administered to a particular muscle of the animal such that the exogenous gene was expressed and the gene product was produced in the particular muscle of the animal. In addition, the adenoviral vector was neutralized outside of the particular muscle of the animal such that there was limited expression of the exogenous gene resulting in production of the gene product outside of the particular muscle of the animal.

For the purposes of this experimental work, C57B1/6 mice were used. The mice were separated into three groups. Systemic neutralizing antibodies were induced in the mice of group 1 with AdNull. AdZ was administered to the mice of groups 1 and 2 iv and im to determine whether production of the reporter gene product β-gal was limited to the right gastrocnemius muscle or could be detected in other areas of the mice, particularly the liver inasmuch as adenoviral vectors are known to localize in the liver after entering the bloodstream of an animal (Jaffee et al., Nat. Genet. 1: 372–78 (1992)). The mice of group 2 were treated as a naive group. Only the adenoviral vector AdZ was administered im and iv to the mice of group 2, i.e., no adenoviral vector was administered to induce systemic neutralizing antibodies in the mice before the administration of the adenoviral vector AdZ. The mice of group 2 otherwise were treated in the same manner as the mice of group 1. Finally, a control group, group 3, which did not receive any administration of adenoviral vectors, was included.

The protocol for administration of the AdNull and AdZ vectors to the mice of the two groups was as follows: the mice of group 1 were immunized with an im injection of $1 \times 10^{10}$ pu of AdNull on day 1 of the experiment, and received a subsequent im or iv injection of $1 \times 10^{10}$ pu of AdZ on day 14. The mice of group 2 (the naive mice) received an injection either iv or im of $1 \times 10^{10}$ pu of AdZ on day 14. The mice of group 3 did not receive any injections.

On day 15, the mice in all three groups were sacrificed. The β-gal activity in the mice was determined in the liver after iv administration of adenoviral gene transfer vector and right gastrocnemius muscle after im administration of the adenoviral gene transfer vector. Neutralizing antibody titers also were determined in the mice. The results of these analyzes are set forth below in Table 1.

TABLE 1

| | β-galactosidase Activity (RLU/mg protein) | | Neutralizing Antibodies (reciprocal dilution) |
|---|---|---|---|
| | Right Gastrocnemius Muscle | Liver | |
| Group 1 (AdNull) | $1.4 \times 10^6$ | $8.1 \times 10^3$ | 32 |
| Group 2 (Naïve) | $4.1 \times 10^6$ | $5.2 \times 10^6$ | 1.0 |
| Group 3 (Control) | $1.1 \times 10^4$ | $7.9 \times 10^3$ | n/a |

As is apparent from the experimental results set forth above, the mice in the first two groups had essentially the same levels of β-gal activity in the right gastrocnemius muscle after im administration of AdZ, about $10^6$ RLU/mg. The mice of group 3 (the control group) had a β-gal activity level of about $10^4$ RLU/mg. The results demonstrate that there was gene expression in the targeted muscle, even in the mice of group 1, which were the subject of the repeat administration.

Moreover, the mice of group 1, in which systemic neutralizing antibodies were induced, had significantly less β-gal activity in the liver when AdZ was administered iv, about $10^4$ (or a hundred-fold less than measured in the target muscle after im administration of the adenoviral gene transfer vector and approximately the same as the control), thereby demonstrating that there was localization of the targeted gene product to the targeted muscle in accordance with the present invention. In distinct contrast, the mice of group 2, in which neutralizing antibodies were not induced, had essentially the same level of β-gal activity in the liver after iv administration of AdZ, about $10^6$ RLU/mg, as in the targeted muscle after im administration of AdZ, thereby indicating that, in the absence of the present inventive method, there is undesirable leaking of the adenoviral vector outside the targeted muscle and wide-spread production of the gene product of interest.

Example 3

This example demonstrates that targeting production of a gene product to a particular muscle in an animal, as well as repeat administration to produce a gene product in a skeletal muscle, is not strain-dependent.

Balb/c mice were used because they mount strong immune responses to both α1-antitrypsin and factor IX, resulting in transient transgene expression (Barr et al., supra; Michou et al., supra). Repeat delivery in Balb/c mice, according to the procedure set forth in Example 2, was determined.

TABLE 2

| | β-glalactosidase Activity (RLU/mg protein) | | Neutralizing Antibodies (reciprocal dilution) |
|---|---|---|---|
| | Right Gastrocnemius Muscle | Liver | |
| Group 1 (AdNull) | $2.1 \times 10^7$ | $9.0 \times 10^3$ | 170 |
| Group 2 (Naïve) | $1.6 \times 10^7$ | $4.0 \times 10^5$ | 105 |
| Group 3 (Control) | $3.0 \times 10^4$ | $2.0 \times 10^4$ | 5 |

The results with Balb/c mice mirrored those observed in C57Bl/6 mice. Secondary im administration 14 days following primary immunization resulted in efficient transduction of the muscle, with β-gal expression equivalent to that observed in non-immunized controls (approximately $10^7$ RLU/mg). Neutralizing antibodies that were present in the serum blocked repeat administration to the liver when virus was administered iv (approximately $10^5$ RLU/mg).

These results indicate that targeting production of a gene product and the ability to repeat administration in a particular muscle with adenovirus gene transfer vectors is not strain-dependent.

Example 4

The present example demonstrates targeting of a gene product to a particular muscle in an animal, as well as repeat administration to produce a gene product in a skeletal muscle using an E1-, E3-, E4-deleted adenoviral gene trans fer vector according to the procedure set forth in Example 2, with the exception that AdE4Null was used in place of AdNull.

TABLE 3

| | β-glactosidase Activity (RLU/mg protein) | | Neutralizing Antibodies (reciprocal dilution) |
|---|---|---|---|
| | Right Gastrocnemius Muscle | Liver | |
| Group 1 (AdE4Null) | $7.5 \times 10^6$ | $6.0 \times 10^4$ | 170 |
| Group 2 (Naïve) | $8.5 \times 10^7$ | $1.1 \times 10^6$ | — |
| Group 3 (Control) | $1.0 \times 10^4$ | $2.1 \times 10^4$ | — |

The results with an E1-, E3-, E4-deleted adenoviral gene transfer vector were very similar to those with an E1-, E3-deleted adenoviral gene transfer vector in Example 2. The mice in the first two groups had essentially the same levels of β-gal activity in the right gastrocnemius muscle after im administration of AdZ, between $10^6$–$10^7$ RLU/mg, while the mice of group 1, in which systemic neutralizing antibodies were induced, had significantly less β-gal activity in the liver after iv administration of the adenoviral gene transfer vector, about $10^4$, for E1-, E3-, E4-deleted adenoviral gene transfer vectors.

These results demonstrate that deletions in the adenoviral genome do not alter neutralization of the adenoviral gene transfer vector or targeting of production of a gene product to a particular muscle.

Example 5

This example demonstrates production of the gene product in the particular muscle of the animal.

According to the procedure described in Example 2, the mice were divided into 3 groups. The first group was then divided into 3 separate groups (Groups 1a, 1b, and 1c). Group 1a was immunized with AdNull, group 1b was immunized with AdVEGF, and group 3 was immunized with AdZ. The 3 members of group 1 were then treated according to Example 2 and received either an im or iv injection of AdZ. Also run were control and naive mice according to Example 2.

TABLE 4

| | β-galactosidase Activity (RLU/mg protein) | | Neutralizing Antibodies (reciprocal dilution) |
|---|---|---|---|
| | Right Gastrocnemius Muscle | Liver | |
| Group 1a (AdNull) | $2.0 \times 10^7$ | $13 \times 10^3$ | 185 |
| Group 1b (AdVEGF) | $2.4 \times 10^7$ | $17 \times 10^3$ | 125 |
| Group 1c (AdZ) | $1.5 \times 10^7$ | $15 \times 10^3$ | 190 |
| Group 2 (Naive) | $8.0 \times 10^7$ | $3.5 \times 10^6$ | 25 |
| Group 3 (Control) | $7.0 \times 10^4$ | $7.0 \times 10^3$ | 20 |

Results are shown in Table 4. The first group had essentially the same levels of β-gal activity in the right gastrocnemius muscle after im administration of AdZ, about $10^7$ RLU/mg, such that there was very little variability between the 3 different vectors used in the initial administrations. This demonstrates that production of the gene product in the skeletal muscle of administration is not affected by the particular adenoviral vector initially administered to the skeletal muscle of the animal. Systemic neutralizing antibodies were induced in the mice in response to the 3 different adenoviral vectors used in group 1. These results demonstrate that production of the gene product in the particular muscle of the animal does not depend upon the systemic neutralizing antibodies induced in the animal. In addition, the levels of β-gal activity in the liver after iv administration of the adenoviral gene transfer vector was similar for the 3 members of group 1 (about $10^4$ RLU/mg).

This example demonstrates production of the gene product in the particular muscle of the animal, irrespective of the systemic neutralizing antibodies induced in the animal. This example further demonstrates that production of the gene product in the skeletal muscle of administration is not affected by the particular adenoviral vector initially administered to the skeletal muscle of the animal.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the claims below.

What is claimed is:

1. A method of targeting a gene product to a particular muscle of a mammal comprising (a) inducing in a mammal systemic neutralizing antibodies to a replication-deficient adenoviral gene transfer vector by systemically or intramuscularly administering the adenoviral gene transfer vector to the mammal, (b) directly administering an adenoviral gene transfer vector, which is identical to the adenoviral gene transfer vector in (a) except that it comprises an exogenous gene encoding a gene product, to a particular muscle of the mammal, such that the exogenous gene is expressed and the gene product is produced in the particular muscle of the mammal and the adenoviral gene transfer vector is neutralized outside of the particular muscle of the mammal by the systemic neutralizing antibodies, and (c) subsequently directly administering to muscle cells an adenoviral gene transfer vector, which is identical to the adenoviral gene transfer vector in (b), except that it comprises a chimeric adenoviral coat protein comprising a nonnative amino acid sequence, wherein the chimeric adenoviral coat protein directs entry of the adenoviral gene transfer vector into muscle cells more efficiently than an adenoviral gene transfer vector that is otherwise identical except for comprising a corresponding wild-type adenoviral coat protein and whereupon the exogenous gene is expressed and the gene product is produced in the muscle cells and the adenoviral gene transfer vector is neutralized outside of the muscle cells by the systemic neutralizing antibodies.

2. The method of claim 1, wherein neutralization of the adenoviral gene transfer vector outside the particular muscle of the animal is such that the production of the gene product is at least 90% less than the production of the gene product outside the particular muscle of a naive animal of the same species as the animal after administration of the adenoviral gene transfer vector.

3. The method of claim 2, wherein neutralization of the adenoviral gene transfer vector outside the particular muscle of the animal is such that the production of the gene product is at least 99% less than the production of the gene product outside the particular muscle of a naive animal of the same species as the animal after administration of the adenoviral gene transfer vector.

4. The method of claim 3, wherein neutralization of the adenoviral gene transfer vector outside the particular muscle of the animal is such that the production of the gene product is at least 99.9% less than the production of the gene product outside the particular muscle of a naive animal of the same species as the animal after administration of the adenoviral gene transfer vector.

5. The method of claim 1, wherein the nonnative amino acid sequence consists essentially of from about 3 to about 30 lysines.

6. The method of claim 1, wherein the mammal is a human.

7. A method of producing a gene product in a skeletal muscle of a mammal comprising (a) initially administering a replication-deficient adenoviral gene transfer vector to the skeletal muscle of the mammal, (b) at least seven days after the administration, subsequently administering an adenoviral gene transfer vector, which is identical to the adenoviral gene transfer vector in (a) except that it comprises an exogenous gene encoding a gene product, to the skeletal muscle of the mammal, such that the exogenous gene is expressed and the gene product is produced in the skeletal muscle of the mammal, and (c) subsequently directly administering to skeletal muscle cells an adenoviral gene transfer vector, which is identical to the adenoviral gene transfer vector in (b), except that it comprises a chimeric adenoviral coat protein comprising a nonnative amino acid sequence, wherein the chimeric adenoviral coat protein directs entry of the adenoviral gene transfer vector into skeletal muscle cells more efficiently than an adenoviral gene transfer vector that is otherwise identical except for comprising a corresponding wild-type adenoviral coat protein and whereupon the exogenous gene is expressed and the gene product is produced in the skeletal muscle cells and the adenoviral gene transfer vector is neutralized outside of the skeletal muscle cells by the systemic neutralizing antibodies.

8. The method of claim 7, wherein production of the gene product in the skeletal muscle of the animal as a result of step (b) is at least 10% of production of the gene product in the skeletal muscle of the animal as a result of step (a).

9. The method of claim 8, wherein production of the gene product in the skeletal muscle of the animal as a result of step (b) is at least 50% of production of the gene product in the skeletal muscle of the animal as a result of step (a).

10. The method of claim 9, wherein production of the gene product in the skeletal muscle of the animal as a result of step (b) is the same or substantially the same as production of the gene product in the skeletal muscle of the animal as a result of step (a).

11. The method of claim 7, wherein the nonnative amino acid sequence consists essentially of from about 3 to about 30 lysines.

12. The method of claim 7, wherein the mammal is a human.

* * * * *